(12) United States Patent
Zhou et al.

(10) Patent No.: US 10,532,134 B2
(45) Date of Patent: Jan. 14, 2020

(54) THIXOTROPIC PROCESSING OF MAGNESIUM COMPOSITES WITH A NANOPARTICLES-HALOED GRAIN STRUCTURE FOR BIOMEDICAL IMPLANT APPLICATIONS

(71) Applicants: Drexel University, Philadelphia, PA (US); Georgia Institute of Technology, Atlanta, GA (US)

(72) Inventors: Gongyao Zhou, Wilmington, DE (US); Haibo Gong, Philadelphia, PA (US); Donggang Yao, Lilburn, GA (US)

(73) Assignee: Drexel University, Philadelphia, PA (US)

( * ) Notice: Subject to any disclaimer, the term of this patent is extended or adjusted under 35 U.S.C. 154(b) by 681 days.

(21) Appl. No.: 14/391,179

(22) PCT Filed: Apr. 18, 2013

(86) PCT No.: PCT/US2013/037153
§ 371 (c)(1),
(2) Date: Oct. 8, 2014

(87) PCT Pub. No.: WO2013/158869
PCT Pub. Date: Oct. 24, 2013

(65) Prior Publication Data
US 2015/0079148 A1  Mar. 19, 2015

Related U.S. Application Data

(60) Provisional application No. 61/635,278, filed on Apr. 18, 2012.

(51) Int. Cl.
| | |
|---|---|
| A61L 31/12 | (2006.01) |
| C22B 26/22 | (2006.01) |
| C22C 1/00 | (2006.01) |
| C22C 23/00 | (2006.01) |
| C22F 1/06 | (2006.01) |
| A61L 27/42 | (2006.01) |
| C22C 1/10 | (2006.01) |
| C22C 26/00 | (2006.01) |
| C22C 32/00 | (2006.01) |
| C22C 23/02 | (2006.01) |
| C22C 23/06 | (2006.01) |

(52) U.S. Cl.
CPC ........... *A61L 31/124* (2013.01); *A61L 27/425* (2013.01); *A61L 27/427* (2013.01); *A61L 31/123* (2013.01); *C22B 26/22* (2013.01); *C22C 1/00* (2013.01); *C22C 1/1036* (2013.01); *C22C 23/00* (2013.01); *C22C 23/02* (2013.01); *C22C 23/06* (2013.01); *C22C 26/00* (2013.01); *C22C 32/00* (2013.01); *C22F 1/06* (2013.01); *A61L 2400/12* (2013.01)

(58) Field of Classification Search
None
See application file for complete search history.

(56) References Cited

U.S. PATENT DOCUMENTS

| | | | |
|---|---|---|---|
| 5,501,748 | A | 3/1996 | Gjestland et al. |
| 6,652,967 | B2 | 11/2003 | Yadav et al. |
| 7,388,042 | B2 | 6/2008 | Yadav et al. |
| 7,824,462 | B2 | 11/2010 | Webster et al. |
| 8,172,908 | B2 | 5/2012 | Ip et al. |
| 8,382,824 | B2 | 2/2013 | Weber |
| 2008/0000557 | A1 | 1/2008 | Ghosh et al. |
| 2010/0320417 | A1 | 12/2010 | Yadav et al. |
| 2011/0006218 | A1 | 1/2011 | Mochalin et al. |
| 2011/0030855 | A1* | 2/2011 | Bharadwaj ............... C22C 23/02 148/538 |
| 2012/0046732 | A1 | 2/2012 | Silekens et al. |
| 2012/0184655 | A1 | 7/2012 | Pullini |
| 2012/0209402 | A1 | 8/2012 | Ip et al. |
| 2012/0241670 | A1 | 9/2012 | Bae et al. |
| 2012/0251742 | A1 | 10/2012 | Kerber |
| 2013/0028781 | A1 | 1/2013 | Xu |
| 2013/0059074 | A1 | 3/2013 | Xu et al. |

FOREIGN PATENT DOCUMENTS

| | | |
|---|---|---|
| CN | 101524559 | 9/2009 |
| WO | WO 2009/038850 | 3/2009 |

OTHER PUBLICATIONS

CN 101524559 (2009) with English translation.*
Pramatarova et al. 2007 (J. Phys.: Conf. Ser. 93 012049).*
Zhang et al. (Biomaterials 32 (2011) 87-94).*
Ye et al. (J Mater Sci: Mater Med (2010) 21:1321-1328).*
PCT/US2013/037153—International Search Report and Written Opinion. dated Jun. 7, 2013.
Moore, Elizabeth Armstrong, "New surgical bone screw biodegrades in two years", CNET News, http://news.cnet.com/8301-27083_3-10461572-247.html, Mar. 1, 2010, 5 pages.

* cited by examiner

*Primary Examiner* — Patricia Duffy
*Assistant Examiner* — Garen Gotfredson
(74) *Attorney, Agent, or Firm* — Joseph E. Maenner; Maenner & Associates, LLC (57) ABSTRACT

In described embodiments, the present invention includes a magnesium-based composite material formed from a plurality of α-phase magnesium grains; and a β-alloy phase comprising magnesium and nano-diamond and/or and phosphate containing nanoparticles, the β-alloy phase surrounding each of the plurality of magnesium grains. A method of manufacturing a composite material is also disclosed.

7 Claims, 9 Drawing Sheets

THIXOTROPIC PROCESSING OF MAGNESIUM COMPOSITES WITH A NANOPARTICLES-HALOED GRAIN STRUCTURE FOR BIOMEDICAL IMPLANT APPLICATIONS

CROSS-REFERENCE TO RELATED APPLICATIONS

This application claims the benefit of the filing date of PCT patent application no. PCT/US2013/037153, filed on Apr. 18, 2013, which claims the benefit of U.S. provisional application No. 61/635,278, filed on Apr. 18, 2012, the teachings of both of which are incorporated herein by reference.

BACKGROUND OF THE INVENTION

1. Field of the Invention

The present invention relates to a magnesium-based composite material that may be used to manufacture implanted medical devices, along with a mixer and a process used to manufacture the composite material.

2. Description of the Related Art

Numerous types of implanted devices, such as plates, screws, pins, stents, rods, anchors, and staples are used in orthopedic, spinal and vascular surgery, e.g., for bone fracture fixation, ankle stabilization, replacement of intervertebral discs, and cardiovascular inflation. The need of such implanted devices is huge and growing with an aging population. For example, for anterior cruciate ligament reconstruction only, more than 90,000 surgeries performed annually worldwide.

Currently, most implanted surgical devices are made primarily of titanium and stainless steel. While these materials have sufficient strength and rigidity to allow the healing process to begin, they are essentially neutral in vivo and are not biodegradable. These permanent fixtures result in adverse effects, such as tissue growth restriction, accumulation of metals in tissues, implant palpability, potential for cross contamination, among other negative impacts. Often, a secondary operation is needed to remove the devices, bringing more pain to the patient. This has led to increasing interest in the development of biodegradable polymer implants, made mainly of poly(lactic acid), poly(glycolic acid) and their copolymers. Biodegradable polymer implants have many advantages, e.g., no long-term implant palpability and temperature sensitivity, predictable degradation, and no stress shielding, leading to better tissue healing, reduced patient trauma, elimination of second surgery for implant removal, and no imaging interference. However, the relatively poor mechanical properties of polymer implants generate frequent surgical failures during installation and/or subsequent use. While efforts have been made to improve the mechanical properties of biopolymers, the effects are moderate since the basic stiffness and strength of polymers are orders of magnitude lower than those of metals. For this reason, polymer implants are not used widely or have limited use in less critical, secondary fixation applications.

Magnesium (Mg) has great potential as a strong and biodegradable material for implant fixation applications because the metal biodegrades and has mechanical properties matching the natural skeletal structure of the human body. The primary problem hampering the actual use of Mg in implanted devices is its extremely rapid degradation rate, losing mechanical integrity within a couple of weeks, rather than the months required for a tissue to fully heal. Furthermore, hydrogen gas is produced as a byproduct of the degradation process, which in small quantities is harmless, but can overwhelm host tissue if produced too quickly.

The primary factor behind rapid Mg-degradation rates is that the resulting oxides are porous, non-stoichiometric, and conduct electricity. By comparison, metals like aluminum, titanium, chromium, and tantalum form oxides that are non-porous, stoichiometric and do not conduct electricity, thus they are corrosion-resistant. Although alloying can be used to reduce degradation rates of Mg, known formulations of these Mg alloys include aluminum or other toxic elements, and therefore are not suitable for medical applications. Alternatively, organic and inorganic materials can be used to coat implants and delay degradation. For example, calcium phosphates (CaP) including hydroxyapatite (HA), tri-calcium phosphate, and calcium hydrogen phosphate (CaHP) have been found to be effective coating materials for Mg. However, coating alone does not lead to desired biodegradable devices; because once the coating layer is consumed, rapid degradation starts with the generation of large amounts of hydrogen gas. Therefore, magnesium-based materials with tunable degradation rates are needed.

BRIEF SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a magnesium-based composite material comprising a plurality of $\alpha$-phase magnesium grains and a $\beta$-alloy phase comprising magnesium, nano-diamond particles, and nano-phosphate particles, the $\beta$-alloy phase surrounding each of the plurality of magnesium grains.

Additionally, the present invention provides a method of forming a magnesium-based composite material. The method comprises the steps of providing magnesium in a thixotropic mixer; heating the magnesium above the magnesium $\alpha$-phase temperature, thereby obtaining a fully molten liquid; lowering the temperature of the magnesium below the magnesium $\alpha$-phase temperature, but above the magnesium $\beta$-phase temperature; mixing the magnesium to obtain a slurry with high solid faction; adding nanoparticles to the slurry; mixing the nano particle-added slurry; and discharging the mixture from the mixer.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

Magnesium (Mg) has great potential as a fixation material in implanted medical devices because it degrades in body fluids and has mechanical properties that match those of the natural human skeletal structure. However, existing Mg-based materials either degrade too quickly or are toxic. The present invention is a novel biocompatible Mg composite with a nanoparticles-haloed grain structure that has enhanced corrosion resistance suitable for implanted medical devices, such as skeletal fixation tools, vascular inflation stents, and bone tissue engineering scaffolds.

Figure 1A:
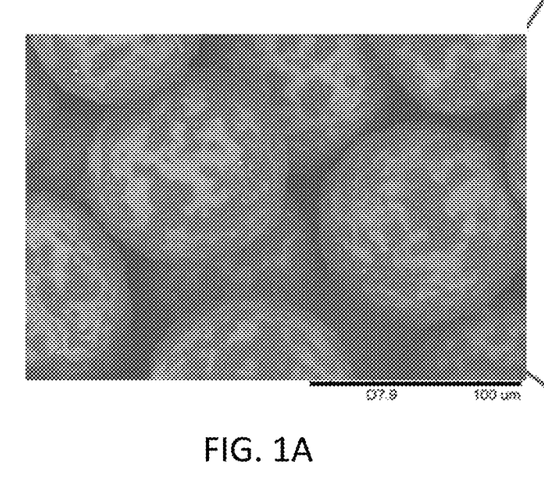
FIG. 1A shows a photograph of a Mg composite with a nano diamond-haloed grain structure according to an exemplary embodiment of the present invention.

The inventive Mg-based composite material has a nanoparticles-haloed grain structure, as shown in FIG. 1A. With this design, only limited nanoparticles are needed to form a corrosion-resistant internal barrier for Mg. There are two primary crystalline phases of Mg in the composite; one is the α-Mg phase and the other is the β-alloy phase. The β-phase has a distinctly lower melting temperature (between about 470 and about 550 degrees C.) than the α-phase (between about 580 and about 640 degrees C.) so that during novel thixotropic mixing (described below), only the β-phase will be melted and nanoparticles will be mixed only into the β-phase. In a proven biocompatible Mg/Ca alloy, the β-phase melting temperature is about 80° C. lower than that of the α-phase. The Mg/Ca alloy is safe in animal systems, although the degradation rate is still more rapid than (toxic) Mg/Al alloys. The inventive approach is to reduce particle loading; instead of directly mixing CaP nanoparticles in the matrix, nano-diamond (ND) particles are incorporated as a seeding material in the composite design. Once exposed to body fluid, ND works as a nucleating agent for precipitation of CaP. ND particles terminated with carboxyl groups serve as strong nucleating sites for CaP precipitation and a phosphate layer can be formed in a short period.

The inventive material design not only reduces the consumption of nanoparticles but also leads to a dense passivation layer formed on individual Mg grains. This mechanism is fundamentally different from that used in current Mg nanocomposites, where pure Mg is still presented between phosphate particles and forms a path for corrosion. The inventive material design also largely benefits from the rich chemistry already developed for functionalizing ND particles. As shown FIG. 1B, it is known that functional groups including hydroxyl group (OH), carboxyl group (COOH), and other carbonyl groups (or their combinations) can be appended to a single ND particle through wet or gas chemistry. Most of these functional groups, particularly OH and COOH, can survive at elevated temperatures above 600° C. for a long time in an oxygen-depleted environment.

Figure 2:
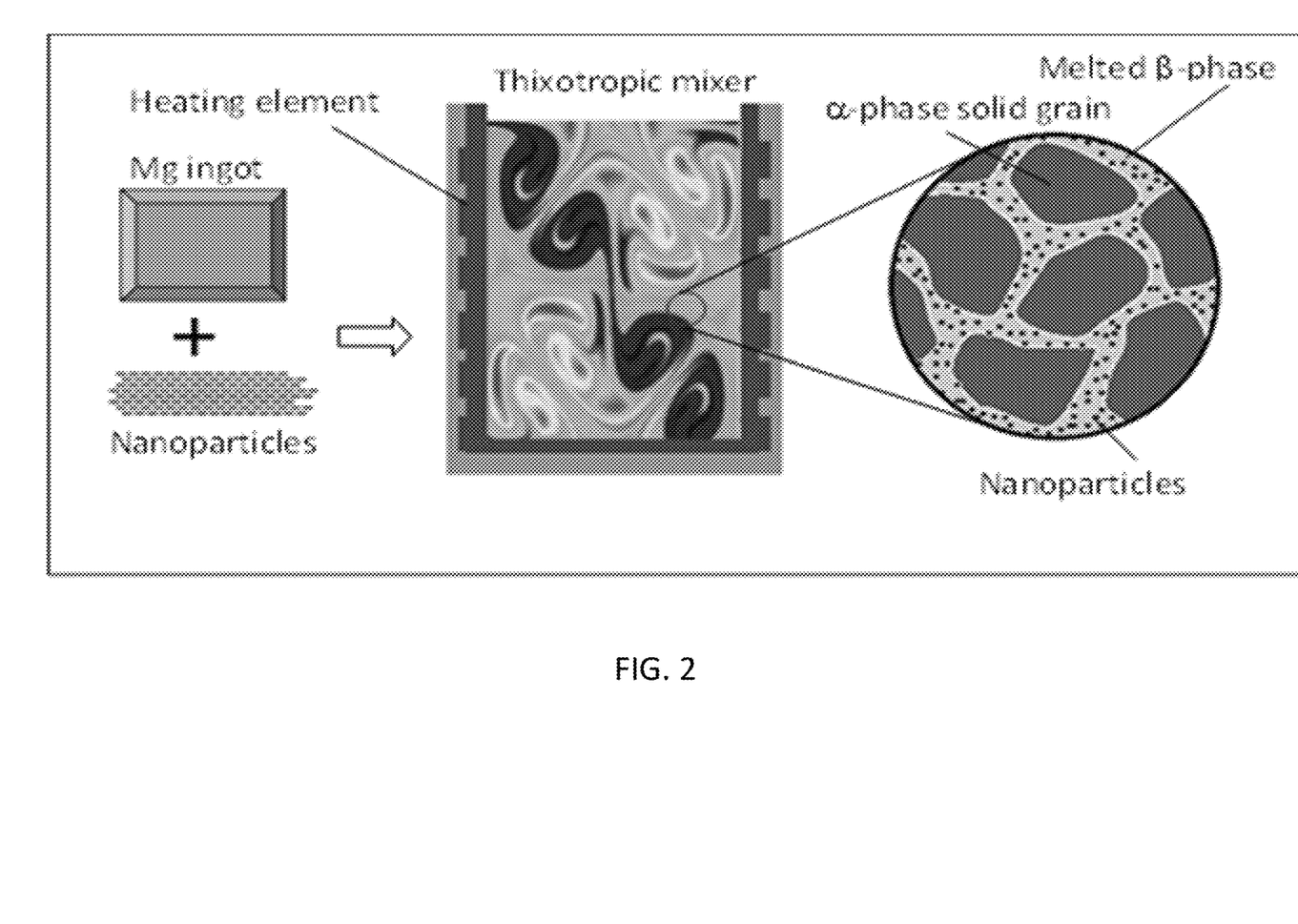
FIG. 2 shows a schematic thixotropic mixing process according to an exemplary embodiment of the present invention.

The inventive Mg nanocomposite is processed using an innovative thixotropic mixing process as illustrated in FIG. 2. This thixotropic process is introduced to produce a special nanoparticle-haloed grain structure and further produce necessary shear stress for dispersive mixing. During thixotropic processing, Mg is processed as a slurry with micro-sized solid grains suspended in the melt. This is facilitated by the inclusion of two distinct melting temperatures in the Mg so that the α-phases remain as solid grains and the nanoparticles are only dispersed into the liquid β-phases. Another advantage of thixotropic mixing is the large shear stress generated due to the relatively high viscosity of the slurry, as well as grain-to-grain mechanical interactions. This mechanism of mixing bears some similarity to ball milling and yet is able to create a consolidated material after mixing. In an exemplary method using ball mixing and sintering to create ND-haloed Mg composites and, with between about 1 percent and about 30 percent loading, a three time improvement in corrosion resistance was achieved. Additional improvement is provided by optimizing if the ND functionalization and the thixotropic mixing process for better dispersion is employed. Thixotropic processing employs a lower processing temperature and significantly higher pressure than a prior art casting method, resulting in lower thermal shrinkage and better consolidation, producing a corrosion-resistant material less vulnerable to voids. Although thixotropic processing has been used for over two decades for casting and molding of Mg alloys, the inventors believe that the use of the thixotropic state for increasing stress in dispersive mixing and creating a nanoparticles-haloed composite structures is new.

ND particles with sizes between 2 and 10 nm have been synthesized by various techniques including detonation, laser ablation, high-energy ball milling, plasma-assisted CVD and ion/electron irradiation. Especially, detonated ND nanoparticles are available in large quantities and represent a new class of relatively inexpensive carbon nanomaterial with a broad range of potential applications. A variety of wet and gas chemistry techniques are known to tailor the properties of ND particles for use in composites and also for applications such as attachment of drug and biomolecules. Additionally, in vitro and in vivo studies have been conducted to examine the biological characteristic of ND particles as diverse as cell viability, gene program activity, and in vivo mechanistic and physiological behavior. These studies generally reported that ND particles are biocompatible and cause minimal cell cytotoxicity. Essentially, ND is considered the most biocompatible material among all known carbon derived nanomaterials.

Figure 1B:
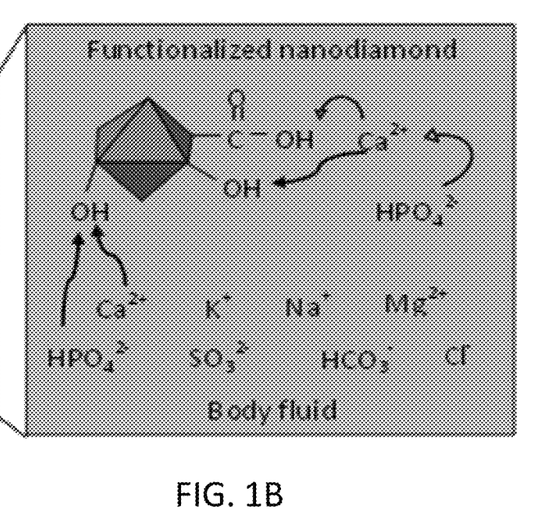
FIG. 1B shows a schematic drawing of an exemplary functionalized nano diamond used to form the nano diamond-haloed grain structure shown in FIG. 1B.

In the inventive composite and method, ND is used as a new corrosion inhibiting material for Mg alloys. It has been shown that COOH terminated ND induced rapid deposition of CaP (confirmed by infrared spectroscopy) from simulated body fluids (SBF). It is believed by the inventors that the functional groups on ND favorably interact with the calcium cation in the SBF which in turn attract the phosphate anion, as illustrated in FIG. 1B. Since CaP is a known corrosion inhibiting material and represents an essential ingredient in the bone, the inventors hypothesize that ND particles with suitable surface chemistry can serve as an effective corrosion-resistant nanofiller to Mg alloy.

The surface of detonated ND is initially terminated with a variety of groups including OH, COOH and C=O groups. Known procedures for refining functional groups are followed to produce ND with COOH-rich or OH-rich terminations.

Compared with Mg/CaP nanocomposites that rely on a large quantity of CaP for improving corrosion resistance, the inventive approach using ND as a seed for CaP holds a new promise for generating corrosion resistant Mg composites with significantly lower nanoparticle loading. There are several unique characteristics of ND making it suitable for serving as a nucleating site. First, the surface of ND can be easily functionalized to render the necessary chemistry for mineralization. Second, ND particles can be refined within a small size range between 2 and 10 nm, while the size of commercial CaP nanoparticles varies from 20 to a few hundred nanometers. Further, CaP particles are typically a mixture containing HA, CaHP and beta-tricalcium phosphate having different crystalline structures. Therefore, ND particles with richer chemistry, smaller size and well defined crystalline structure may serve as a more reliable nucleating agent for generation of a denser CaP passivation layer.

Figure 3:
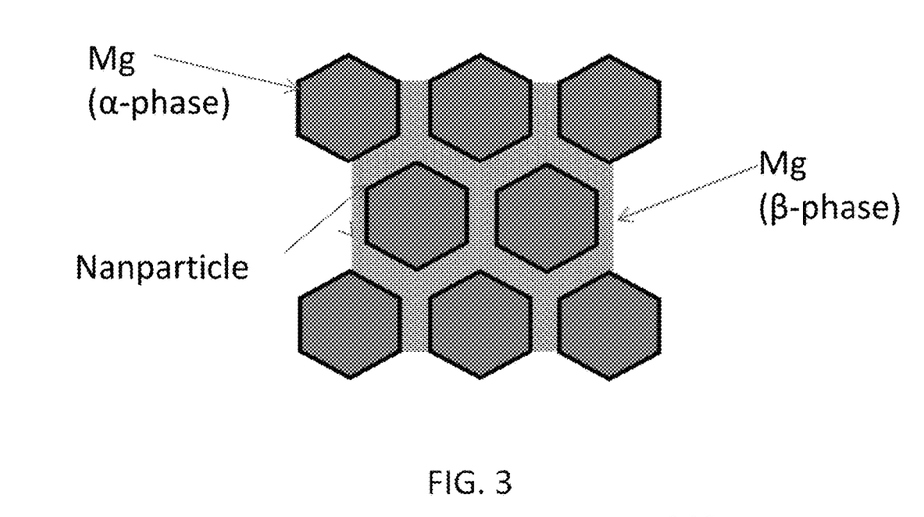
FIG. 3 shows a schematic drawing of an exemplary nano particle-haloed grain structure according to the present invention.

Therefore, a dispersed intergranular structure, with grains uniformly haloed by dispersed nanoparticles, as shown in FIG. 3, is desired.

To obtain the inventive nanoparticles-haloed grain structure through mechanical mixing, an inventive apparatus and method capable of (1) generating a semisolid slurry with good fluidity, (2) producing extremely high shear and high pressure for mixing, and (3) rapidly controlling the cooling rate is required. The first characteristic is needed for achieving low nanoparticle loading with necessary processability. As a result, the inventive mixer is required to handle a large fraction of solid grains in the semisolid. This is accomplished by the second characteristic, the high pressure and high shear capability. The shear motion helps break the dendritic structure and produce globular grains inside the slurry. From the non-Newtonian flow behavior of suspensions, it is also believed that the viscosity of the slurry decreases with increasing shear amplitude. The high pressure and high shear are also beneficial to the generation of a denser material, reducing the porosity caused by shrinkage, a common problem in low-pressure melt casting processes. Furthermore, the nanoparticle dispersion is greatly enhanced by high-shear high-pressure semisolid processing. The third characteristic of rapid cooling is necessary for in situ thermomechanical control so that a refined grain structure is obtained.

The thixotropic mixing concept uses the phenomenon that Mg alloys with two distinct liquidus temperatures can be processed as high-viscosity plastic materials using slightly modified polymer processing equipment such as an injection molding machine. This marriage between melt casting and polymer/plastic molding creates many new opportunities to the metal processing industry. However, prior art thixomolding machines cannot easily fulfill all three characteristics stated above. In particular, the dwell time in an injection molding machine is short and therefore precision control of the thermomechanical history to achieve the necessary structural evolution and intergranular nanoparticle dispersion is difficult. Therefore, inventors have developed a laboratory mixer 100 with better thermal mechanical controls, as shown in FIGS. 4A-4D. The major components of this apparatus are made of high-temperature tungsten alloys, and the torque and pressure for driving the mixer are supplied by an external torque generator and a hydraulic press.

Figures 4A, 4B:
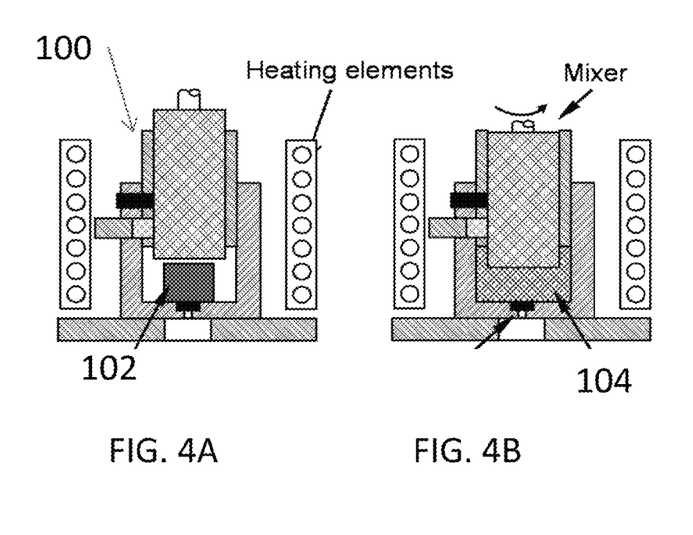
FIG. 4A shows a thixotropic mixer with the Mg ingot inserted therein according to an exemplary embodiment of the present invention.
FIG. 4B shows the thixotropic mixer of FIG. 4A, with the Mg ingot heated below the α-phase melting temperature above the β-phase melting temperature, forming a slurry.
Figure 4C:
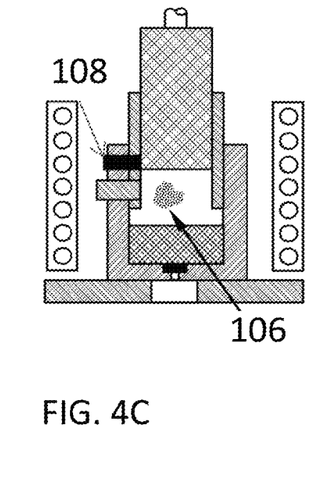
FIG. 4C shows the thixotropic mixer of FIG. 4A, with nanoparticles inserted therein.
Figure 4D:
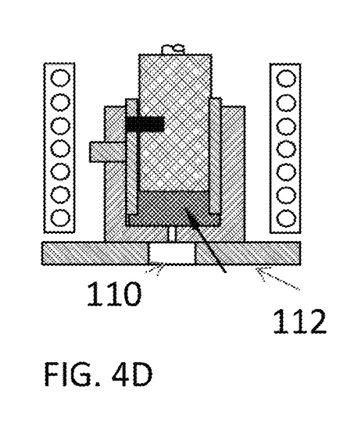
FIG. 4D shows the thixotropic mixer of FIG. 4A, with the nanoparticles mixed into the slurry.

Four steps are involved. First, a Mg ingot 102 is heated above the α-phase melting temperature to obtain a fully molten liquid. Second, the temperature is lowered below the α-phase melting temperature but above the β-phase melting temperature, and intensive mixing is applied to obtain a slurry 104 with high solid faction, as shown in FIG. 4B. Next, nanoparticles 106 are added into the slurry 104 through a side feeder 108, as shown FIG. 4C. Finally, after sufficient mixing, the mixture is discharged from a discharge port 110 on a lower support plate 112, as shown in FIG. 4D. During the entire operation, argon is used for oxidation protection. The thermal design for achieving rapid heating and cooling is an important feature of this mixer. Particularly, the discharged material can be rapid quenched into a cooling medium, such as room temperature oil, for preserving the morphology, or may be injected into plaques for further characterization. The rotor in the inventive mixer is used both as an agitator for mixing and as a plunger for material discharging. Mixing effects may be improved by including some intensive (known) mixing elements at the end of the rotor.

Figure 5:
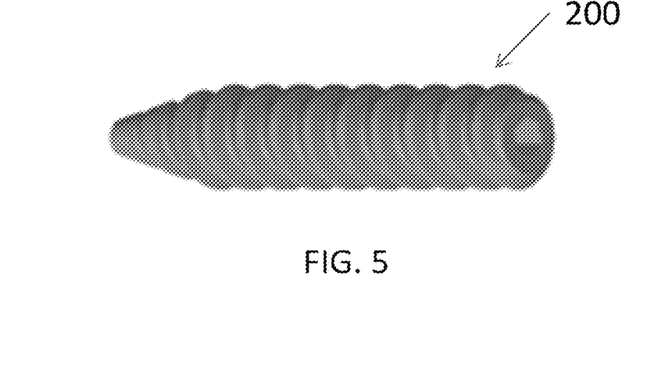
FIG. 5 shows an implantable screw, manufactured using the inventive composite and the inventive method.

A bone-fixation interference screw 200 with overall length about 25 mm, shown FIG. 5, was chosen as a testing device. A prior art screw is made of poly(lactic acid) with a modulus more than 10 times lower than that of Mg. For this purpose, the inventors set the target degradation time to be 12 months. The material parameters including α-phase to β-phase ratio and nanoparticle loading are adjusted and the thixotropic mixing conditions are optimized for achieving the necessary performance criteria.

Figure 6:
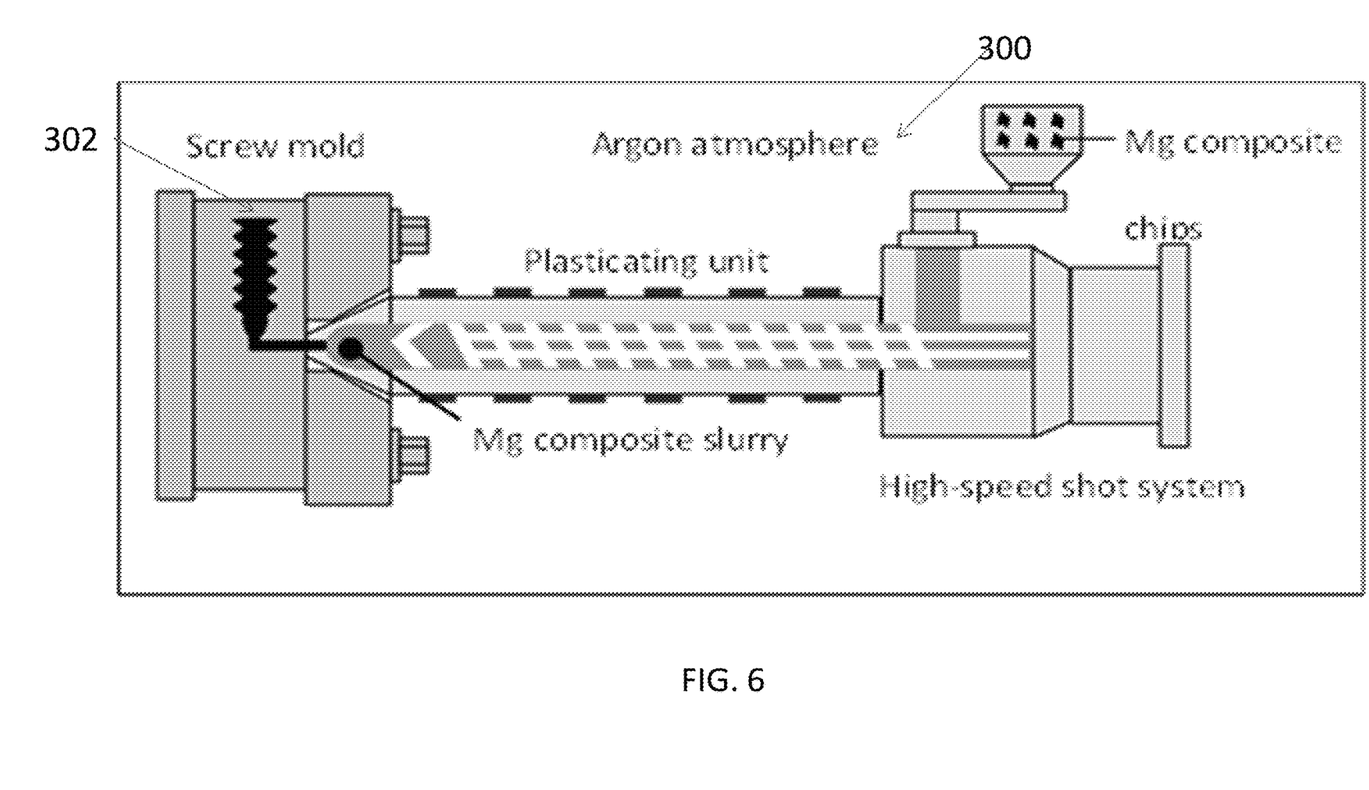
FIG. 6 shows a schematic diagram of an injection molding process used to manufacture the screw, shown FIG. 5.

The Mg composite material discharged from the thixotropic mixer, in threads or plaques, are mechanically shredded into small chips. The thixomolding injection molding process, as schematically illustrated in FIG. 6, is used for molding these Mg composite chips into interference screws. During thixomolding, the Mg composite material is heated just above the α-phase melting and injected into the mold cavity 302 in an injection thixomolding device 300 as a slurry with high solid faction. This high-pressure high-shear semisolid molding process has a number of advantages over melt casting processes such as die casting. Less shrinkage, reduced porosity, and improved surface finish and dimensional accuracy are achieved with thixomolding.

In addition to setting the temperature to only melt the β-phase and not thea-phase, it is also important to tune the screw action in the injection unit such that the original morphology with the haloed structure is largely retained during melting and injection of the materials. A short melting time (i.e., several minutes) and injection time (i.e., several seconds) are helpful to minimize thermomechanical influences on morphological evolution.

Figure 7:
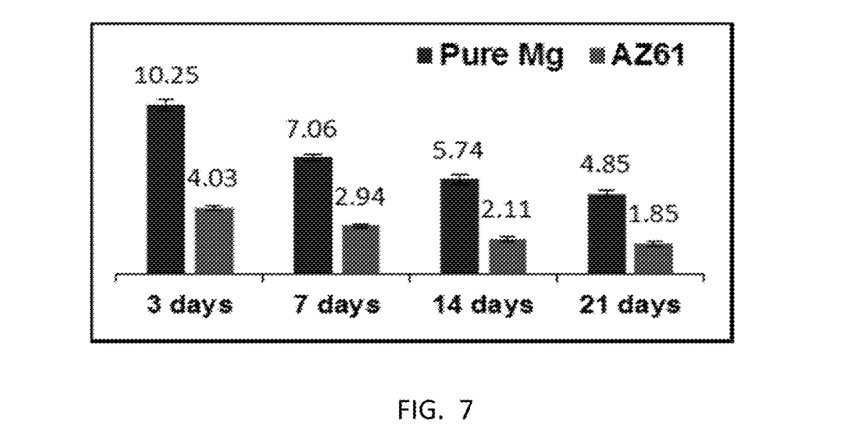
FIG. 7 shows a corrosion rate of pure Mg compared to Mg alloy AZ61.

Extruded pure (commercial grade) Mg (99.9% purity) and AZ61 (Mg93/Al6/Zn1) alloy were evaluated in terms of corrosion resistance by immersion test in SBF (ASTM-G31-72) and mechanical properties by tensile test (ASTM-E8-04). As shown in FIG. 7, the corrosion rate of the alloy is much lower compared with the pure Mg. The tensile test results are summarized in Table 1.

TABLE 1

|  | Elastic modulus (GPa) | Yield strength (MPa) |
|---|---|---|
| Cortical Bone | 3-20 | 35-283 |

TABLE 1-continued

|  | Elastic modulus (GPa) | Yield strength (MPa) |
|---|---|---|
| Titanium | 115 | 480 |
| Poly-lactic acid | 3 | 80 |
| Pure Mg | 46 | 90 |
| Mg alloy AZ61 | 46 | 204 |

The elastic modulus and yield strength of Mg are closer to those of natural bone than other commonly used metallic and biopolymer implants. The relatively poor mechanical properties of biopolymeric surgical fixation devices generate frequent surgical breakage during insertion and/or subsequent failure. In contrast, the elastic moduli of current metallic biomaterials are not well matched with that of natural bone tissue, resulting in stress shielding effects that can lead to reduced stimulation of new bone growth and remodeling which decreases implant stability. These results demonstrated useful mechanical properties of Mg and its alloys; however, their corrosion resistance needs to be improved for actual applications in biomedical implants.

Figure 8A:
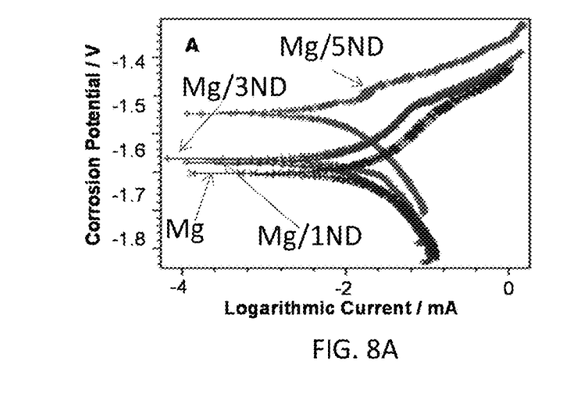
FIG. 8A shows a graph of logarithmic potential of pure Mg compared to Mg alloys.
Figure 8B:
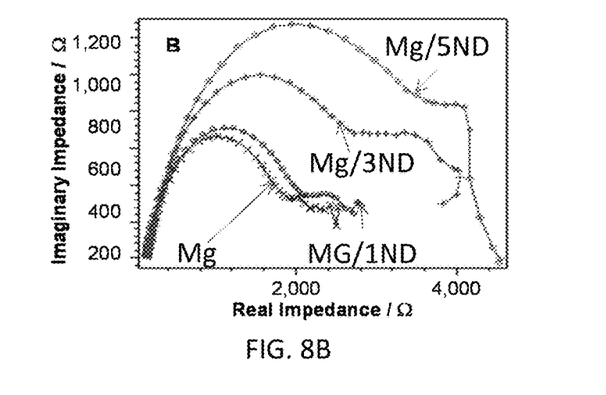
FIG. 8B shows a graph of potential electrical impedance scan of pure Mg compared to Mg alloys.

Detonated ND particles were purified and then air oxidized above 400° C. to obtain COOH functional groups on the ND surface. Four Mg/ND nanocomposites (Mg, Mg/1ND, Mg/3ND, Mg/5ND, in wt %) prepared by ball milling and powder metallurgy were tested to compare their corrosion related properties in SBF. Linear polarization (LP) curves and potential electrochemical impedance scan (PEIS) curves are shown in FIGS. 8A and 8B, respectively. A higher corrosion potential in LP curve and a larger loop in PEIS curve indicate a lower average corrosion rate of the material. Table 2 lists corrosion rates from immersion test and the corrosion potential and resistance derived from FIGS. 8A and 8B.

TABLE 2

|  | Pure Mg | Mg-1% ND | Mg-3% ND | Mg-5% ND |
|---|---|---|---|---|
| Corrosion rate (mg/cm$^2$/h) | 2.93 ± 0.060 | 1.66 ± 0.094 | 1.03 ± 0.085 | 0.65 ± 0.068 |
| Corrosion potential (V) | −1.55 | −1.67 | −1.68 | −1.70 |
| Resistance (Ohm) | 2796 | 2919 | 4279 | 5059 |

It is seen that Mg nanocomposite with higher ND loading had lower corrosion rate, higher corrosion potential, and higher electrical resistance. Specifically, the corrosion rate of Mg-5% ND was reduced by 4.5 times by adding 5 wt % of ND particles.

Figure 9A:
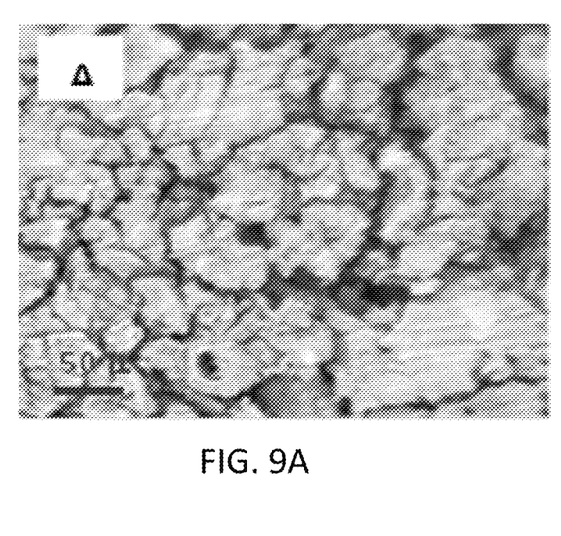
FIG. 9A shows a photograph of corroded Mg after being submerged in simulated body fluid for one day.
Figure 9B:
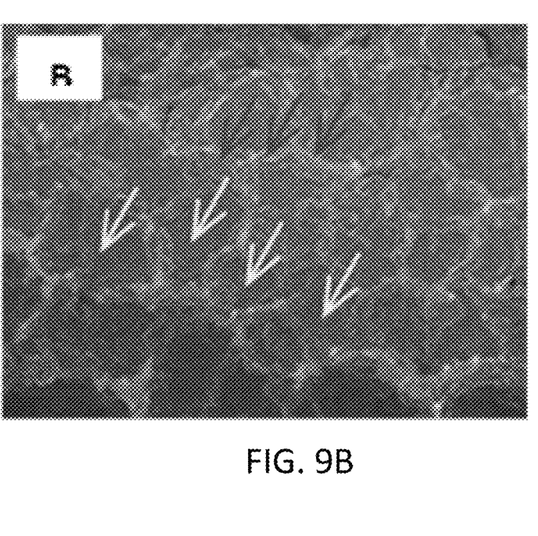
FIG. 9B shows a photograph of a Mg composite, manufactured according to the present invention after being submerged in simulated body fluid the same time period as the Mg, shown FIG. 7A.
Figure 10A:
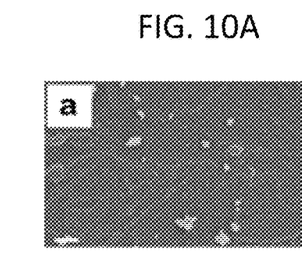
FIG. 10A shows a scanning electron microscope (SEM) micrograph showing mineral formation on neat PLLA after three days.
Figure 10B:
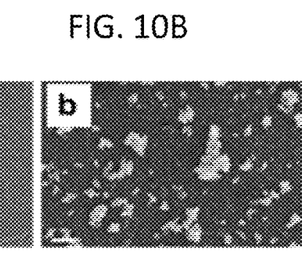
FIG. 10B shows an SEM micrograph showing mineral formation on the neat PLLA of FIG. 10A after one week.
Figures 10C, 10D, 10E:
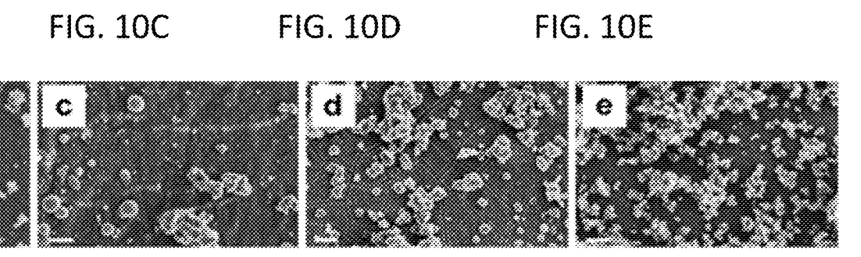
FIG. 10C shows an SEM micrograph showing mineral formation on the neat PLLA of FIG. 10A after two weeks.
FIG. 10D shows an SEM micrograph showing mineral formation on the neat PLLA of FIG. 10A after four weeks.
FIG. 10E shows an SEM micrograph showing mineral formation on the neat PLLA of FIG. 10A after six weeks.
Figures 10F, 10G:
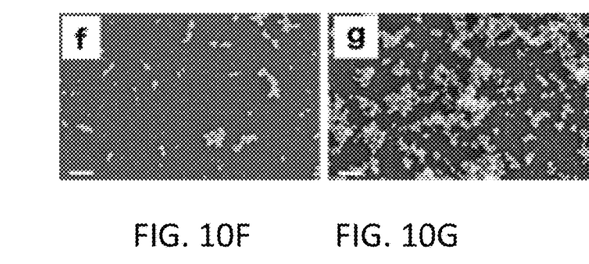
FIG. 10F shows an SEM micrograph showing mineral formation on PLLA with a 10% nano diamond composite after three days.
FIG. 10G shows an SEM micrograph showing mineral formation on the PLLA with a 10% nano diamond composite of FIG. 10E after one week.
Figures 10H, 10I:
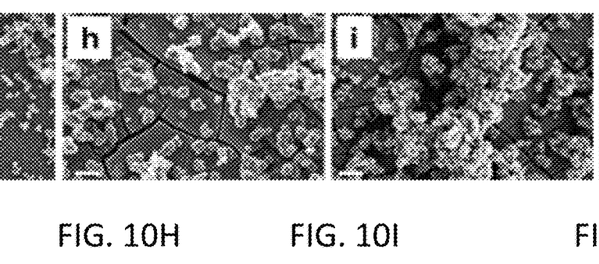
FIG. 10H shows an SEM micrograph showing mineral formation on the PLLA with a 10% nano diamond composite of FIG. 10E after two weeks.
FIG. 10I shows an SEM micrograph showing mineral formation on the PLLA with a 10% nano diamond composite of FIG. 10E after four weeks.
Figure 10J:
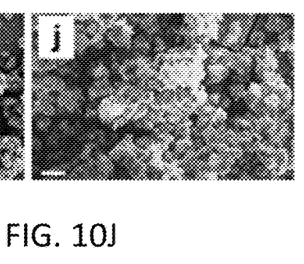
FIG. 10J shows an SEM micrograph showing mineral formation on the PLLA with a 10% nano diamond composite of FIG. 10E after six weeks.

FIG. 9A shows the surface morphology of pure Mg after being submerged in SBF for 1 day. High corrosion led to formation of deep surface cracks. In comparison, the surface of the Mg/5ND composite was coated with a deposited layer when submerged in SBF for the same period, as shown in FIG. 9B. The samples were prepared by ball milling and sintering, and the grains (on yellow arrows) and grain boundary (on red arrows) can be clearly seen. It is interesting to note that there appeared to be more deposition at the grain boundary as seen by the small humps formed. The Mg/ND composite was sintered at 350° C., which is below the melting temperature of Mg. Therefore, it is expected that ND particles should be rich at the grain boundary. This leads to the formation of an ND-haloed grain structure. The ND particles at the grain boundary then work as nucleating sites for mineralization.

To minimize the chemical effect of matrix material, a relatively inert biopolymer PLLA was selected as matrix and ND particles were uniformly distributed inside. The PLLA-ND composite with different ND content was then immersed in SBF to investigate the corrosion inhibiting mechanism of ND particles. FIG. 10A-10J show representative SEM images of neat PLLA and PLLA-10% ND composite immersed in SBF for 3 days, 1, 2, 4 and 6 weeks, respectively. The number and size of mineral particles and their size increased with the incubation time and the concentration of ND in the PLLA matrix. The weight of mineral particles formed on PLLA-ND was significantly ($p<0.05$) larger than that on the neat PLLA for the same SBF incubation time. A typical FTIR spectrum of the mineral particles scratched from PLLAND surface showed peaks at 564, 604, and 1035 $cm^{-1}$ that can be attributed to $PO_4^{3-}$ groups. These results suggested that ND promoted the deposition of phosphates in SBF.

Besides the thixomolding process described above, a powder metallurgy (PM) process may be used to achieve the inventive nano-haloed grain structure in a Mg nano-composite. The PM method has been applied to create both Mg-ND and nano-phosphate composite with a nano-haloed grain structure. Results showed significant improvement of Mg's corrosion resistance by adding 0.2~5 w.t. % of ND and nano-phosphate.

Steps of the PM process include packing Mg particles, nano-particles, milling balls and other milling media in an inert environment. The particles are mixed using a high energy ball milling machine. The mixed particles are compacted and sintered using a Cold Isotropic Pressing (CIP), Hot Isotropic Pressing (HIP), Vacuum Hot Pressing (VHP), Powder Forging (PF) or Spark Plasma Sintering (SPS) technique. Deformation processing, such as extrusion, forging, rolling or rotary swaging is applied to the resulting material.

An alternative processing method is ultrasonicator-assisted melting stirring (UMS), which achieves a nano-haloed structure through controlled metal solidification. Nanoparticles are uniformly dispersed in a Mg alloy through the UMS process. The UMS process is an effective way to achieve a uniform Mg nano-composite, and in some cases a majority of nanoparticles cover the Mg grains and form a similar grain structure as the inventive nano-haloed grain structure. While this phenomenon is not clearly understood, the inventors believe that nanoparticle distribution is strongly affected by the metal solidification process. The UMS process with a controlled solidification process can simultaneously achieve both uniform nanoparticle distribution and nano-haloed grain structure.

Figure 11:
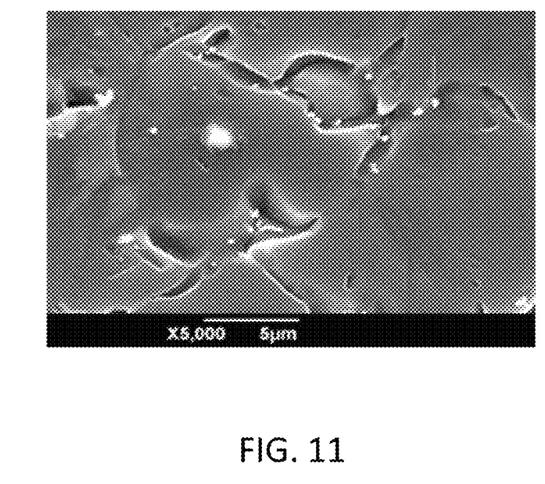
FIG. 11 shows a photograph of a magnesium alloy nano-diamond composite fabricated by an ultrasonicator-assisted melting starring process.

Basic steps of UMS process include providing an inert operation environment and melting a Mg alloy at a temperature between about 530 degrees Celsius and about 780 degrees Celsius. Nanoparticles in powder form or Mg-nano-composite master form are fed into the melted Mg alloy. The melted Mg alloy is start using a known mechanical stirring machine. An ultrasonicator is applied to the melted Mg alloy and the mixed Mg nano-composite is cast in a mold. A magnesium alloy nano-diamond composite fabricated using the UMS process is shown FIG. 11. The arrow in the figure shows the nano-diamond particle.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A magnesium-based composite medical implant comprising:
    a crystalline structure of α-phase magnesium grains; and
    a β-alloy phase comprising magnesium and a combination of functionalized nano-diamond particles and calcium phosphate nanoparticles, wherein the β-alloy phase forms a halo around each of the α-phase magnesium grains.

2. The composite medical implant according to claim 1, wherein the functionalized nano-diamond comprises a functional group selected from the group consisting of hydroxyl group, a carboxyl group, a carbonyl group, and a combination thereof.

3. The composite medical implant according to claim 1, wherein each of the functionalized nano-diamonds has a size range between about 2 nm and less than 5 nm.

4. The composite medical implant according to claim 1, wherein each of the nano-phosphate particles has a size range between about 20 nm and about 300 nm.

5. The composite medical implant according to claim 1, wherein the β-alloy phase comprises about 5% by weight of nanodiamonds.

6. A magnesium-based composite medical implant formed by a process comprising the steps of:
    providing magnesium in a thixotropic mixer;
    heating the magnesium above the magnesium α-phase temperature, thereby obtaining a fully molten liquid;
    lowering the temperature of the fully molten liquid below the magnesium α-phase temperature, but above the magnesium β-alloy phase temperature to form a melt;
    mixing the melt to obtain a slurry comprising solid α-phase magnesium grains suspended in a magnesium β-alloy phase;
    adding functionalized diamond and calcium phosphate nanoparticles to the slurry; and
    mixing the nanoparticle-added slurry in a mixer to form a mixture; and
    discharging the mixture from the mixer,
    wherein the β-alloy phase forms a halo around each of the α-phase magnesium grains wherein the α-phase magnesium grains are formed in a crystalline structure.

7. A magnesium-based composite medical implant comprising:
    a crystalline structure of α-phase magnesium grains; and
    a β-alloy phase consisting essentially of magnesium and a combination of functionalized nano-diamond particles and calcium phosphate nanoparticles, wherein the β-alloy phase forms a halo around each of the α-phase magnesium grains.

* * * * *